US010687952B2

(12) United States Patent
Petranto

(10) Patent No.: US 10,687,952 B2
(45) Date of Patent: Jun. 23, 2020

(54) FLEXIBLE, CANNULATED IMPLANTS FOR THE HAND AND FOOT AND METHODS OF IMPLANTING FLEXIBLE IMPLANTS

(71) Applicant: Russell D. Petranto, Seaside Park, NJ (US)

(72) Inventor: Russell D. Petranto, Seaside Park, NJ (US)

( * ) Notice: Subject to any disclaimer, the term of this patent is extended or adjusted under 35 U.S.C. 154(b) by 93 days.

(21) Appl. No.: 15/891,580

(22) Filed: Feb. 8, 2018

(65) Prior Publication Data

US 2018/0161170 A1    Jun. 14, 2018

Related U.S. Application Data

(60) Provisional application No. 62/615,781, filed on Jan. 10, 2018, provisional application No. 62/614,527, filed on Jan. 8, 2018.

(51) Int. Cl.
*A61F 2/42* (2006.01)
*A61B 17/72* (2006.01)
(Continued)

(52) U.S. Cl.
CPC ........ *A61F 2/4225* (2013.01); *A61B 17/7291* (2013.01); *A61B 17/848* (2013.01);
(Continued)

(58) Field of Classification Search
CPC ............ A61F 2/4225; A61F 2002/4228; A61F 2002/423; A61F 2002/4233;
(Continued)

(56) References Cited

U.S. PATENT DOCUMENTS 3,462,765 A    8/1969  Swanson
3,593,342 A    7/1971  Niebauer
(Continued)

FOREIGN PATENT DOCUMENTS

SU    1296147 A2  *  3/1987    .......... A61F 2/4241

OTHER PUBLICATIONS

International Search Report issued in corresponding International Patent Application No. PCT/US19/12743, dated Apr. 15, 2019, 2 pages.

*Primary Examiner* — David H Willse
*Assistant Examiner* — Javier G Blanco
(74) *Attorney, Agent, or Firm* — Doherty IP Law Group

(57) ABSTRACT

A flexible, cannulated bone implant includes a proximal stem having a proximal end, a distal end, and a proximal conduit extending from the proximal end to the distal end of the proximal stem, a distal stem having a proximal end, a distal end, and a distal conduit extending from the proximal end to the distal end of the distal stem, and a flexible hinge interconnecting the distal end of the proximal stem with the proximal end of the distal stem for allowing the proximal and distal stems to flex relative to one another. The implant includes a proximal stem protective tube disposed within the proximal conduit of the proximal stem, and a distal stem protective tube disposed within the distal conduit of the distal stem. An elongated pin extends through the distal stem protective tube disposed within the distal stem and the proximal stem protective tube disposed within the proximal stem for securing the implant to bone.

12 Claims, 12 Drawing Sheets

(51) Int. Cl.
  *A61F 2/30* (2006.01)
  *A61B 17/84* (2006.01)
  *A61F 2/46* (2006.01)

(52) U.S. Cl.
  CPC ......... *A61F 2/30965* (2013.01); *A61F 2/4606* (2013.01); *A61F 2002/30069* (2013.01); *A61F 2002/30153* (2013.01); *A61F 2002/30154* (2013.01); *A61F 2002/30607* (2013.01); *A61F 2002/30624* (2013.01); *A61F 2002/30772* (2013.01); *A61F 2002/4233* (2013.01)

(58) Field of Classification Search
  CPC ............ A61F 2002/4235; A61F 2/4241; A61F 2002/4243; A61F 2002/4246; A61F 2002/4248; A61B 17/7291
  See application file for complete search history.

(56) References Cited

U.S. PATENT DOCUMENTS

| | | | |
|---|---|---|---|
| 3,745,590 A * | 7/1973 | Stubstad | A61F 2/30907 623/13.11 |
| 3,886,600 A * | 6/1975 | Kahn | A61F 2/30907 623/20.24 |
| 3,875,594 A | 8/1975 | Swanson | |
| 4,158,893 A * | 6/1979 | Swanson | A61F 2/4241 623/18.11 |
| 4,204,284 A | 5/1980 | Koeneman | |
| 4,246,662 A | 1/1981 | Pastrick | |
| 4,313,232 A | 2/1982 | Habal et al. | |
| 4,367,562 A | 1/1983 | Gauthier | |
| 4,578,080 A * | 3/1986 | Helal | A61F 2/30721 606/155 |
| D291,731 S | 9/1987 | Aikins | |
| 4,871,367 A | 10/1989 | Christensen et al. | |
| 4,908,031 A | 3/1990 | Frisch | |
| 5,824,095 A | 10/1998 | DiMaio, Jr. et al. | |
| 6,319,284 B1 * | 11/2001 | Rushdy | A61F 2/4225 623/18.11 |
| 6,475,242 B1 | 11/2002 | Bramlet | |
| D490,900 S | 6/2004 | Ogilvie et al. | |
| 6,869,449 B2 * | 3/2005 | Ball | A61F 2/4241 623/21.11 |
| 7,951,198 B2 | 5/2011 | Sucec et al. | |
| 8,529,611 B2 | 9/2013 | Champagne et al. | |
| 8,597,337 B2 | 12/2013 | Champagne | |
| 8,617,227 B2 | 12/2013 | Sucec et al. | |
| 8,852,284 B2 | 10/2014 | Wiley et al. | |
| 8,945,232 B2 | 2/2015 | Sander et al. | |
| 9,138,274 B1 | 9/2015 | Biesinger et al. | |
| 9,504,582 B2 | 11/2016 | Sander et al. | |
| 2003/0069645 A1 | 4/2003 | Ball et al. | |
| 2007/0185583 A1 * | 8/2007 | Branemark | A61F 2/4241 623/18.11 |
| 2011/0004255 A1 | 1/2011 | Weiner et al. | |
| 2011/0005454 A1 | 3/2011 | Champagne et al. | |
| 2012/0065692 A1 | 3/2012 | Champagne et al. | |
| 2013/0190830 A1 | 7/2013 | Champagne et al. | |
| 2015/0073413 A1 * | 3/2015 | Palmer | A61B 17/7266 606/63 |
| 2015/0223942 A1 * | 8/2015 | Merle | A61F 2/4241 623/21.15 |
| 2017/0007416 A1 | 1/2017 | Sander et al. | |

* cited by examiner

FLEXIBLE, CANNULATED IMPLANTS FOR THE HAND AND FOOT AND METHODS OF IMPLANTING FLEXIBLE IMPLANTS

CROSS-REFERENCE TO RELATED APPLICATIONS

The present patent application claims benefit of U.S. Provisional Application No. 62/615,781, filed Jan. 10, 2018, and U.S. Provisional Application No. 62/614,527, filed Jan. 8, 2018, the disclosures of which are hereby incorporated by reference herein.

BACKGROUND OF THE INVENTION

Field of the Invention

The present patent application is generally related to surgical implants, and is more specifically related to implants for hand digital implantation and treating hammertoe deformities.

Description of the Related Art

A hammer toe is a deformity that causes a toe to bend or curl downward instead of pointing forward. This deformity can affect any toe on a foot. It most often affects the second, third, and fourth toe.

Hammer toe most frequently results from wearing poorly fitting shoes that can force the toe into a bent position, such as excessively high heels or shoes that are too short or narrow for the foot, thereby disrupting the muscle tendon balance of the proximal interphalangeal joint (hereinafter referred to as "the PIP joint") and the metatarsophalangeal joint (hereinafter referred to as "the MTP joint"). Having the toes bent for long periods of time can cause the muscles in them to shorten, resulting in the hammer toe deformity. This is often found in conjunction with bunions or other foot problems (e.g., a bunion can force the big toe to turn inward and push the other toes). It can also be caused by muscle, nerve, or joint damage resulting from conditions such as osteoarthritis, rheumatoid arthritis, stroke, Charcot-Marie-Tooth disease, complex regional pain syndrome or diabetes. Hammer toe deformities can also be found in Friedreich's ataxia (GAA trinucleotide repeat). https://en.wikipedia.org/wiki/Hammer_toe.

In many cases, conservative treatment consisting of physical therapy, padding techniques, and new shoes with soft, spacious toe boxes is enough to resolve the condition. In more severe or longstanding cases hammertoe surgery may be necessary to correct the deformity. In some instances, an implant is placed into the toe to correct the hammer toe deformity.

There have been a number of efforts directed to providing implants for treating hammer toe deformities. For example, Wright Medical Group N.V. of Memphis, Tenn. sells implants and implant kits for treating hammer toe deformities under the trademark PHALINX™. Some of the implants are cannulated so that Kirschner wires may be passed through cannulated openings for securing implants to bone. Other implants have a ten degree angle designed into the implant so that a toe carrying the implant may have a slight bend instead of being held in a permanent, straight orientation. In any event, the implants are rigid and do not flex, which results in toes being locked in position and unable to post-operatively flex and bend. Moreover, conventional implants do not address both the MTP joint contracture correction while allowing flexion at the PIP joint.

Thus, there remains a need for hammertoe implants that allow toes to post-operatively flex and bend while also allowing surgical correction at the MTP joint. There also remains a need for hammertoe implants having flexible hinges and/or flexible joints so that the proximal and distal stems of the implant may flex and move relative to one another after being implanted in the respective proximal and middle phalanxes of a toe. In addition, there remains a need for flexible, cannulated implants for use in the hand or for being implanted between to bones of a human or animal patient.

SUMMARY OF THE INVENTION

In one embodiment, a flexible, cannulated hammertoe implant preferably provides for surgical correction with stabilization of a hammer toe deformity at a metatarsal phalangeal joint, while allowing flexion at the proximal interphalangeal jointpost-operatively.

In one embodiment, a flexible, cannulated implant is used for hand digital implantation.

In one embodiment, a flexible, cannulated implant is used between two bones of a human or animal patient, whereby the implant allows for post-operative flexibility between the two bones.

The flexible implant may be made of medical grade biocompatible materials that are typically used for making surgical implants including metals (e.g., titanium, stainless steel, alloys thereof), polymers (e.g., plastics, medical grade silicone elastic polymers), and combinations of metals and polymers.

In one embodiment, a hammertoe implant has a central cannulated core that allows for the placement of an elongated pin (e.g., a Kirschner wire), which may be retrograded across the metatarsal phalangeal joint to stabilize the surgical correction of the soft tissue contracture.

In one embodiment, a hammertoe implant has a proximal stem that is adapted for placement into the proximal phalanx and a distal stem that is adapted for placement into the middle phalanx. In one embodiment, the proximal stem is longer than the distal stem.

In one embodiment, a hammertoe implant may be a unitary structure or body having a flexible hinge that is located between and interconnects the proximal stem of the implant and the distal stem of the implant. The flexible hinge is preferably thinner than the proximal and distal stems to provide a more flexible region of the implant. In one embodiment, the flexible hinge may be reinforced with a strut system or one or more reinforcing elements to prevent fracturing of the implant at the hinge. In one embodiment, the reinforcing elements may be made of fabric, fabric mesh, polyester mesh, fabric material sold under the trademark DACRON, or other fabrics that are compatible with the polymers or plastics used to make the unitary body of the implant.

In one embodiment, a hammertoe implant has a cannulated central shaft that allows for the placement of an elongated pin (e.g., a Kirschner wire) for stabilization of the digital deformity post-operatively at the MTP joint. In one embodiment, the elongated pin (e.g., a Kirschner wire) positioned within the cannula may be removed after 4-6 weeks post-operative to allow for flexion at the proximal interphalangeal joint. The elongated pin may have different diameters. In one embodiment, the elongated pin has diameters ranging from 0.035-0.062 inches.

In one embodiment, a flexible bone implant preferably includes a proximal stem having a proximal end, a distal end, and a proximal conduit extending from the proximal end to the distal end of the proximal stem, a distal stem having a proximal end, a distal end, and a distal conduit extending from the proximal end to the distal end of the distal stem, and a flexible hinge interconnecting the distal end of the proximal stem with the proximal end of the distal stem for allowing the proximal and distal stems to flex relative to one another. In one embodiment, the flexible hinge may have one or more reinforcing struts or reinforcing elements to prevent fracturing of the implant at the flexible hinge.

In one embodiment, a flexible bone implant preferably includes a proximal stem protective tube disposed within the proximal conduit of the proximal stem, and a distal stem protective tube disposed within the distal conduit of the distal stem.

In one embodiment, an elongated pin extends through the distal stem protective tube disposed within the distal stem and the proximal stem protective tube disposed within the proximal stem for securing the implant to bone.

In one embodiment, the proximal stem, the distal stem, and the flexible hinge comprise a unitary structure made of polymer materials such as silicone elastic polymers and/or plastics.

In one embodiment, the proximal stem protective tube and the distal stem protective tube are made of metal such as biocompatible metals, titanium, titanium alloys, stainless steel, and/or stainless steel alloys.

In one embodiment, the elongated pin may be bone pins or Kirchner wires of different sizes.

In one embodiment, the proximal stem has a flat top surface, a flat bottom surface, and flat side surfaces that define a proximal stem structure having a substantially square or rectangular shaped cross-section.

In one embodiment, the distal stem has a flat top surface, a flat bottom surface, and flat side surfaces that define a distal stem structure having a substantially square or rectangular shaped cross-section.

In one embodiment, the flexible hinge preferably includes a top side defined by a first sloping sidewall at the distal end of the proximal stem, a second sloping sidewall at the proximal end of the distal stem that opposes the first sloping sidewall, and a flat top surface that extends between and interconnects lower ends of the first and second sloping sidewalls.

In one embodiment, the first sloping sidewall, the second sloping sidewall and the flat top surface define a V-shaped top side of the flexible hinge having a truncated, flat apex.

In one embodiment, the proximal conduit extending through the proximal stem defines a first opening in the first sloping sidewall, and the distal conduit extending through the distal stem defines a second opening in the second sloping sidewall that is aligned with the first opening in the first sloping sidewall.

In one embodiment, the flexible implant is normally urged into a straight configuration in which the proximal and distal conduits extend along a common axis.

In one embodiment, the flexible implant is moveable into a flexed configuration in which the proximal and distal conduits extend along different axes that define an angle.

In one embodiment, the flexible hinge may also include a bottom side defined by a first bottom side sloping sidewall at the distal end of the proximal stem, a second bottom side sloping sidewall at the proximal end of the distal stem that opposes the first bottom side sloping sidewall, and a flat bottom surface that extends between and interconnects upper ends of the first and second bottom side sloping sidewalls.

In one embodiment, the first bottom side sloping sidewall, the second bottom side sloping sidewall, and the flat bottom surface define a V-shaped bottom side of the flexible hinge having a truncated, flat apex.

In one embodiment, a flexible implant may include a reinforcing element embedded within the flexible hinge or covering one or more surfaces of the flexible hinge. In one embodiment, the reinforcing element may be a mesh, such as a polyester mesh. In one embodiment, the polyester mesh may be made of the polyester fabric sold under the trademark DACRON. In other embodiments, other reinforcing fabrics may be used instead of polyester fabrics so long as they are compatible with the polymer or plastic materials used to make the implant.

In one embodiment, a flexible bone implant preferably includes a unitary, polymer body including a proximal stem, a distal stem, and a flexible hinge located between the proximal and distal stems. In one embodiment, the proximal stem has a proximal end, a distal end, and a proximal conduit extending from the proximal end to the distal end of the proximal stem. In one embodiment, the distal stem has a proximal end, a distal end, and a distal conduit extending from the proximal end to the distal end of the distal stem. In one embodiment, the flexible hinge interconnects the distal end of the proximal stem with the proximal end of the distal stem for allowing the proximal and distal stems to flex relative to one another.

In one embodiment, a proximal stem protective tube made of metal is disposed within the proximal conduit of the proximal stem, and a distal stem protective tube made of metal is disposed within the distal conduit of the distal stem.

In one embodiment, the flexible hinge includes a top side defined by a first sloping sidewall at the distal end of the proximal stem, a second sloping sidewall at the proximal end of the distal stem that opposes the first sloping sidewall, and a flat top surface that extends between and interconnects lower ends of the first and second sloping sidewalls.

In one embodiment, the flexible implant may include one or more reinforcing elements in contact with the flexible hinge. The reinforcing element may be a reinforcing fabric embedded within the flexible hinge, and/or covering one or more of the top and bottom surfaces of the flexible hinge for enhancing the durability of the hinge during repeated flexing and bending.

In one embodiment, the proximal conduit extending through the proximal stem defines a first opening in the first sloping sidewall, and the distal conduit extending through the distal stem defines a second opening in the second sloping sidewall that is aligned with the first opening in the first sloping sidewall.

In one embodiment, an elongated pin such as a Kirchner wire extends in series through the proximal stem protective tube disposed within the distal stem, the first opening in the first sloping sidewall, the second opening in the second sidewall, and the proximal stem protective tube disposed within the proximal stem.

In one embodiment, the implant is a unitary, polymer body that normally urges the flexible implant into a straight configuration in which the proximal and distal conduits are in alignment with one another and extend along a common axis. The flexible implant is moveable into a flexed configuration in which the proximal and distal conduits are not in alignment with one another and extend along different axes that define an angle.

In one embodiment, a method of implanting a flexible bone implant in bone preferably includes providing a flexible bone implant including a proximal stem having a proximal end, a distal end, and a proximal conduit extending from the proximal end to the distal end of the proximal stem, a distal stem having a proximal end, a distal end, and a distal conduit extending from the proximal end to the distal end of the distal stem, and a flexible hinge interconnecting the distal end of the proximal stem with the proximal end of the distal stem.

In one embodiment, a method includes forming a distal opening in a distal bone and inserting the distal stem of the flexible bone implant into the distal opening, and forming a proximal opening in a proximal bone and inserting the proximal stem into the proximal opening so that the flexible hinge is located between the proximal and distal bones.

In one embodiment, a method includes flexing the flexible bone implant so that the proximal and distal conduits extend along axes that define an angle, and inserting a distal end of an elongated pin into an opening at a proximal end of the distal conduit and advancing the elongated pin distally through the distal stem and the distal bone so that a distal end of the elongated pin projects out of the end of a toe, finger, or animal appendage.

In one embodiment, a method includes placing the flexible bone implant in a straight configuration so that the proximal and distal conduits extend along a common axis, and inserting a proximal end of the elongated pin into the proximal conduit and advancing the elongated pin proximally (i.e., retrograding the elongated pin) through the proximal stem and the proximal bone.

In one embodiment, a method includes before the inserting the elongated pin into the distal and proximal conduits, disposing a proximal stem protective tube within the proximal conduit of the proximal stem, and disposing a distal stem protective tube within the distal conduit of the distal stem.

In one embodiment, the flexible bone implant is a unitary structure made of polymer materials and the protective tubes are made of biocompatible metals.

In one embodiment, the implant may be made of a polymer or plastic material with the proximal and distal conduits being formed in the respective proximal and distal stems. In one embodiment, the proximal and distal conduits may be hardened by using a polymer or plastic layer that is harder than the polymer or plastic material utilized to make the proximal stem, the distal stem and the flexible hinge of the implant. In one embodiment, the proximal and distal conduits may be treated with a chemical that hardens the conduits for preventing the elongated pin from damaging the surfaces of the conduits as the elongated pin passes through the conduits. In one embodiment, when the proximal and distal conduits are hardened, it may not be necessary to place metal protective tubes within the conduits.

These and other preferred embodiments of the flexible, cannulated implants disclosed herein and methods of implanting the disclosed implants in a patient will be described in more detail herein.

DETAILED DESCRIPTION OF PREFERRED EMBODIMENTS

Figure 1A:
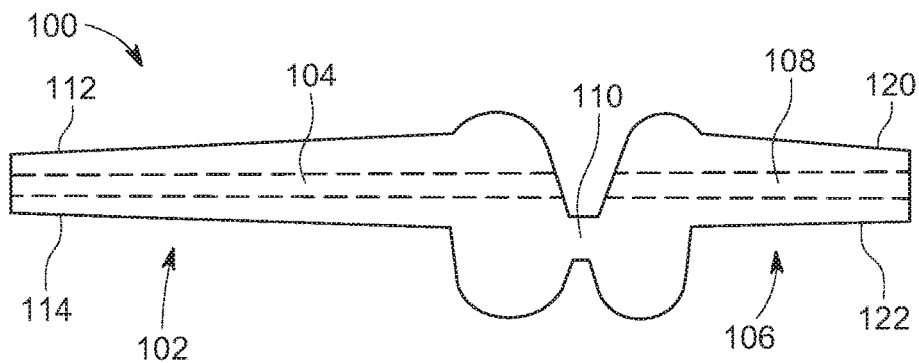
FIG. 1A shows a side view of a flexible implant including a proximal stem, a distal stem, and a flexible hinge that interconnects the proximal and distal stems, in accordance with one embodiment of the present patent application.
Figure 1B:
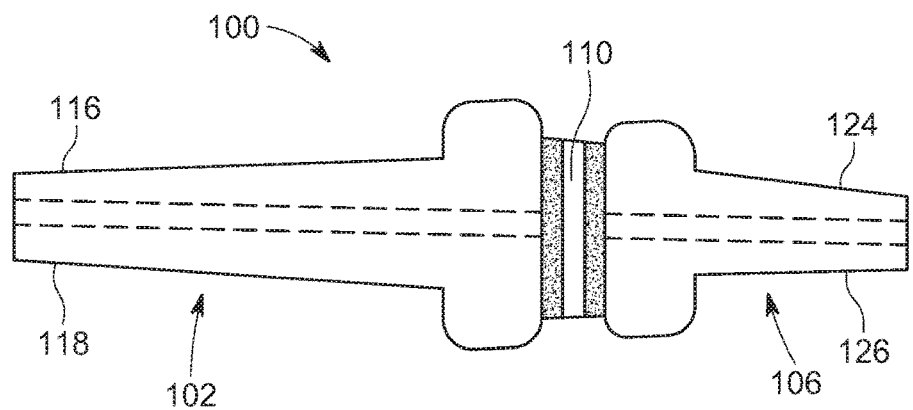
FIG. 1B shows a top plan view of the flexible implant shown in FIG. 1A.

Referring to FIGS. 1A and 1B, in one embodiment, a flexible, cannulated hammertoe implant 100 preferably includes a proximal stem 102 having a proximal conduit 104 extending therethrough, a distal stem 106 having a distal conduit 108 extending therethrough, and a flexible hinge 110 that is located between and interconnects a distal end of the proximal stem 102 and a proximal end of the distal stem 106. In one embodiment, the implant is preferably a unitary polymer or plastic body that includes the proximal stem, the distal stem, and the flexible hinge that interconnects the proximal and distal stems. As will be described in more detail herein, the flexible hinge 110 preferably enables the hammertoe implant 100 to flex and/or bend so that after the implant has been implanted in a toe, the distal stem 106 may rotate, swing and/or move relative to the proximal stem 102. In one embodiment, the flexible hinge 110 is thinner than the proximal and distal stems 102, 106 to provide a region of the implant that is capable of flexing and/or to provide a more flexible region of the implant.

In one embodiment, one or more of the proximal and distal stems 102, 106 may include stabilizing features for securing the stems to bone including but not limited to threads, surface roughening and/or bone engaging fins. In one embodiment, the stabilizing features are preferably provided on the outer surfaces of the proximal and distal stems.

In one embodiment, the implant and/or the flexible hinge may include strengthening struts or a reinforcing element to prevent fracturing of the flexible hinge during flexing and bending. In one embodiment, the reinforcing element may be embedded inside the flexible hinge. In one embodiment, the reinforcing element may be disposed over one or more surfaces of the flexible hinge. In one embodiment, the reinforcing element may be include a first reinforcing fabric embedded within a flexible hinge, with a second reinforcing fabric secured over one of the top and bottom surfaces of the flexible hinge. In one embodiment, the reinforcing element may include a first reinforcing fabric embedded within the flexible hinge, a second reinforcing fabric secured over a top surface of the flexible hinge, and a third reinforcing fabric secured over a bottom surface of the flexible hinge.

In one embodiment, the flexible hammertoe implant 100 may be made of medical grade biocompatible materials that are typically used for making surgical implants including metals (e.g., titanium, stainless steel, alloys thereof), alloys, polymers (e.g., plastics, medical grade silicone elastic polymers), and combinations of metals, alloys and/or polymers. In one embodiment, the implant 100 is made of a combination of metal and polymer materials.

In one embodiment, the proximal stem 102 has a flat top surface 112, a flat bottom surface 114, and flat side surfaces 116, 118 that provide the proximal stem with a substantially square or rectangular shaped cross-section.

In one embodiment, the distal stem 106 has a flat top surface 120, a flat bottom surface 122, and flat side surfaces 124, 126 that provide the distal stem with a substantially square or rectangular shaped cross-section.

Figure 2:
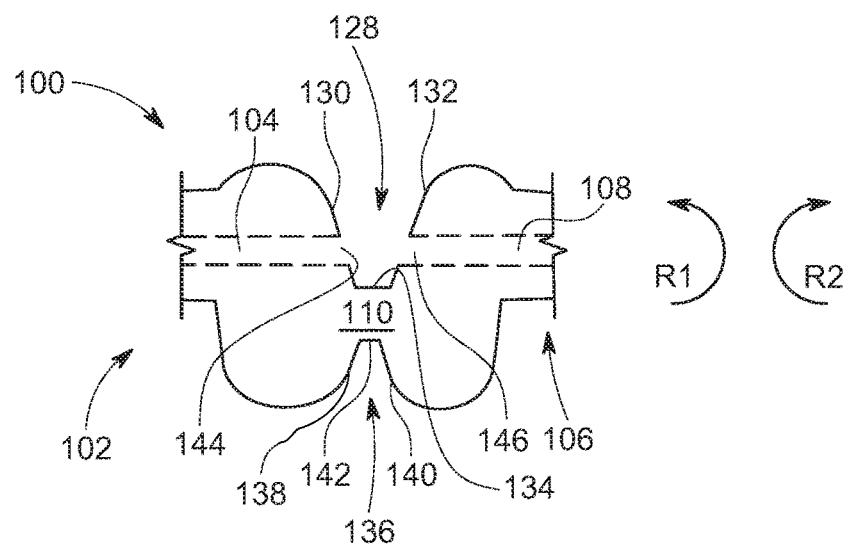
FIG. 2 shows a magnified view of the flexible hinge of the flexible implant shown in FIG. 1A.

Referring to FIG. 2, in one embodiment, the flexible hinge 110 of the implant 100 preferably includes a top side 128 of the hinge 110 defined by a first sloping sidewall 130 at the distal end of the proximal stem 102, a second sloping sidewall 130 at the proximal end of the distal stem 106 (that opposes the first sloping sidewall 130), and a flat top surface 134 that extends between and interconnects lower ends of the first and second sloping sidewalls 130, 132. The first sloping sidewall 130, the second sloping sidewall, and the flat top surface 134 of the top side 128 of the hinge 110 preferably define a V-shaped top side 128 having a truncated, flat apex. In one embodiment, the flat top surface 134 does not come to a point or apex, which enhances the strength of the hinge 110 and minimizes the likelihood that the hinge will fracture and/or crack during flexing and bending of the implant.

In one embodiment, when rotating the distal stem 106 of the implant 100 in a counterclockwise direction R1 relative to the proximal stem 102, the second sloping surface 132 at the proximal end of the distal stem 106 may abut against the first sloping surface 130 at the distal end of the proximal stem 102 for acting as a hard stop and limiting further counterclockwise rotation of the distal stem 106 relative to the proximal stem 102.

In one embodiment, the flexible hinge 110 of the implant 100 preferably includes a bottom side 136 defined by a first sloping sidewall 138 at the distal end of the proximal stem 102, a second sloping sidewall 140 at the proximal end of the distal stem 106 (that opposes the first sloping sidewall 138), and a flat bottom surface 142 that extends between and interconnects upper ends of the first and second sloping sidewalls 138, 140. The first sloping sidewall 138, the second sloping sidewall 140, and the flat bottom surface 142 of the bottom side 136 of the hinge 110 preferably define a V-shaped bottom side 136 having a truncated, flat apex. In one embodiment, the flat bottom surface 142 does not come to a point or apex, which enhances the strength of the hinge 110 and minimizes the likelihood that the hinge will fracture and/or crack during flexing and bending.

In one embodiment, when rotating the distal stem 106 of the implant 100 in a clockwise direction R2 relative to the proximal stem 102, the second sloping surface 140 at the proximal end of the distal stem 106 may abut against the first sloping surface 138 at the distal end of the proximal stem 102 for acting as a hard stop and limiting further clockwise rotation of the distal stem 106 relative to the proximal stem 102.

In one embodiment, the proximal conduit 104 that extends through the proximal stem 102 defines a first opening 144 in the first sloping sidewall 130, and the distal conduit 108 that extends through the distal stem 106 defines a second opening 146 in the second sloping sidewall 132. The first and second openings 144, 146 in the sloping sidewalls are preferably in alignment with one another when the implant is straight so that an elongated pin (e.g., a Kirschner wire) may be passed through the aligned proximal and distal conduits 104, 108.

Figure 3A:
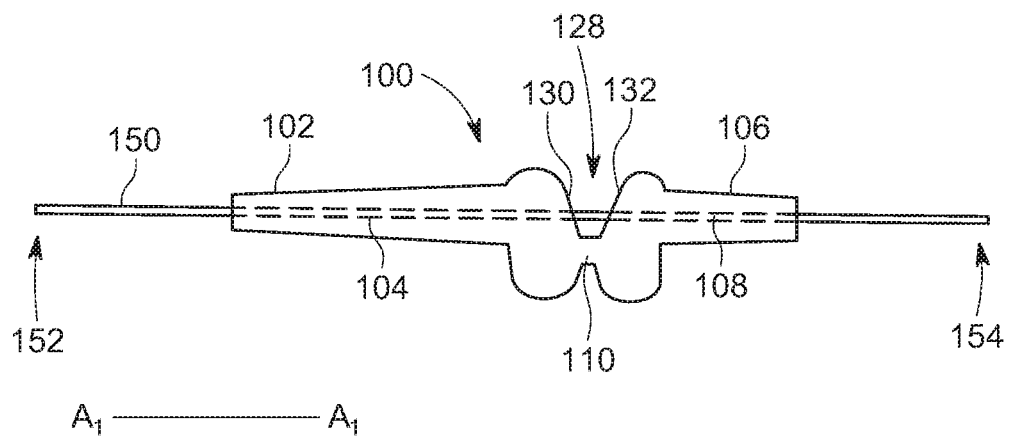
FIG. 3A shows a side view of the implant of FIG. 1A with an elongated pin extending through the proximal and distal stems, in accordance with one embodiment of the present patent application.
Figure 3B:
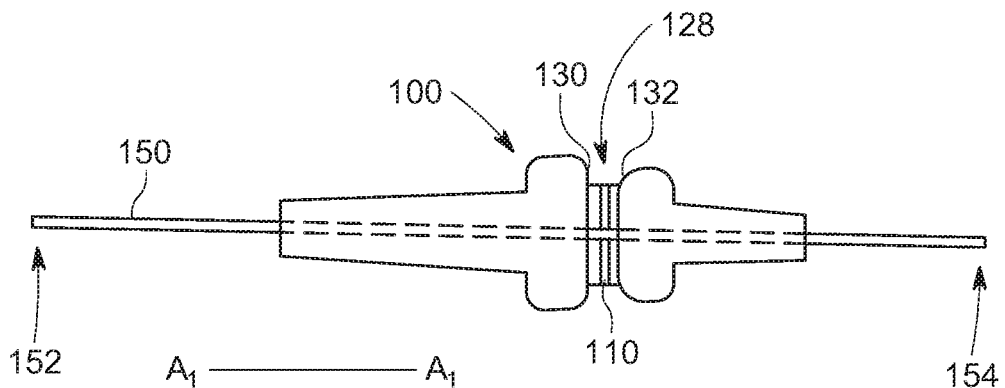
FIG. 3B shows a top plan view of the implant and the elongated pin shown in FIG. 3A.
Figure 4A:
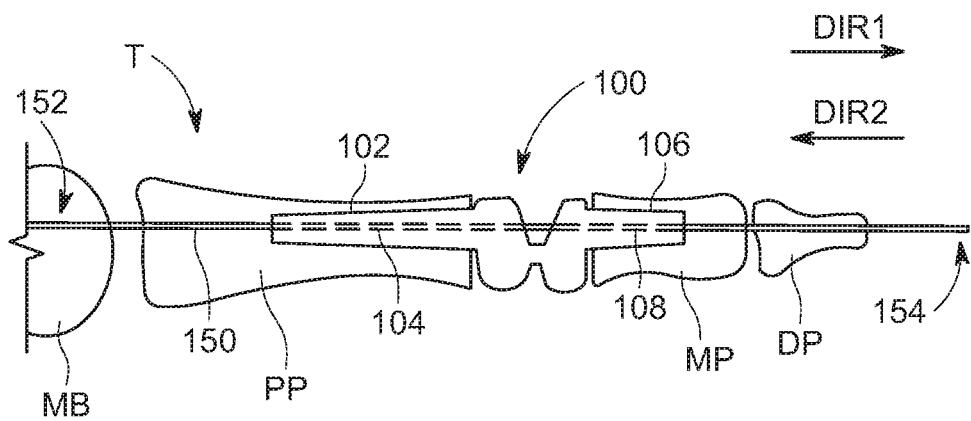
FIG. 4A shows a cross-sectional side view of the bones of a toe with the flexible implant and elongated pin of FIG. 3A implanted in the osseous structure of the toe, in accordance with one embodiment of the present patent application.
Figure 4B:
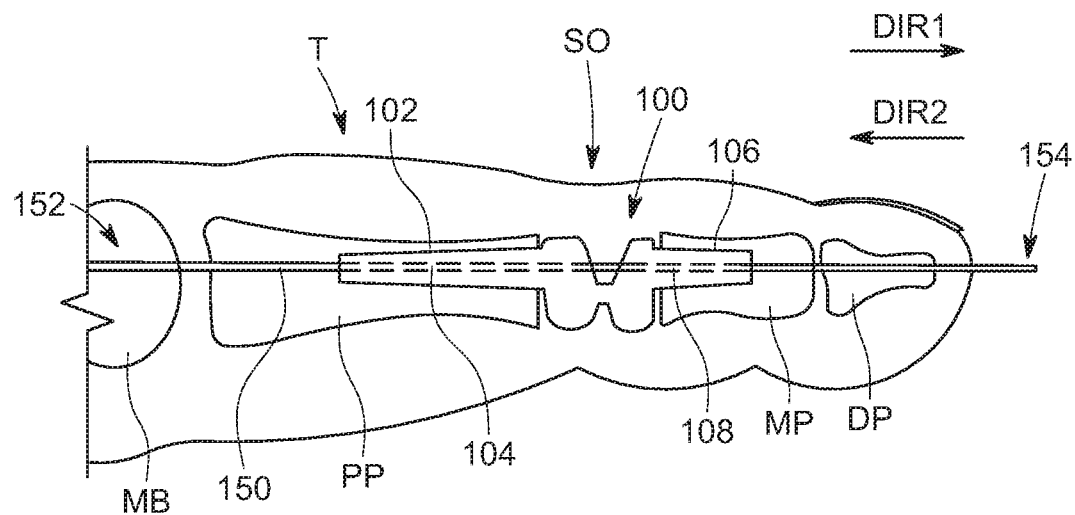
FIG. 4B shows another cross-sectional side of the flexible implant and the elongated pin shown in FIG. 4A.
Figure 5A:
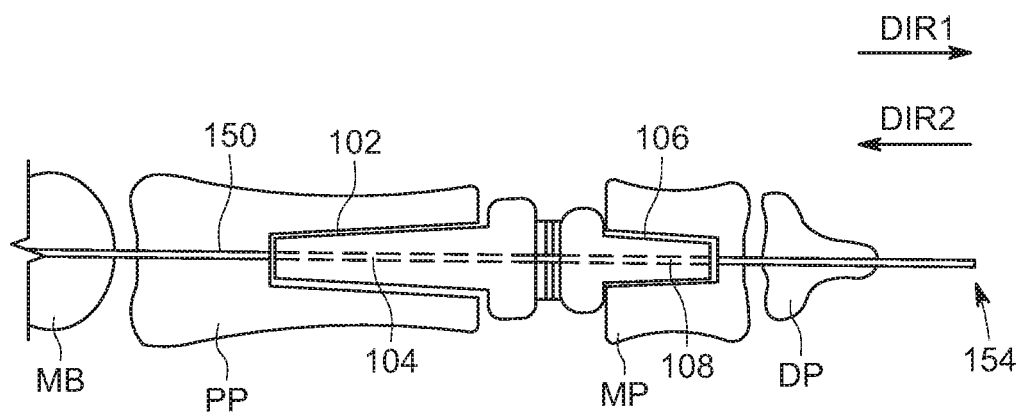
FIG. 5A shows a cross-sectional top plan view of the flexible implant and the elongated pin of FIG. 4A.
Figure 5B:
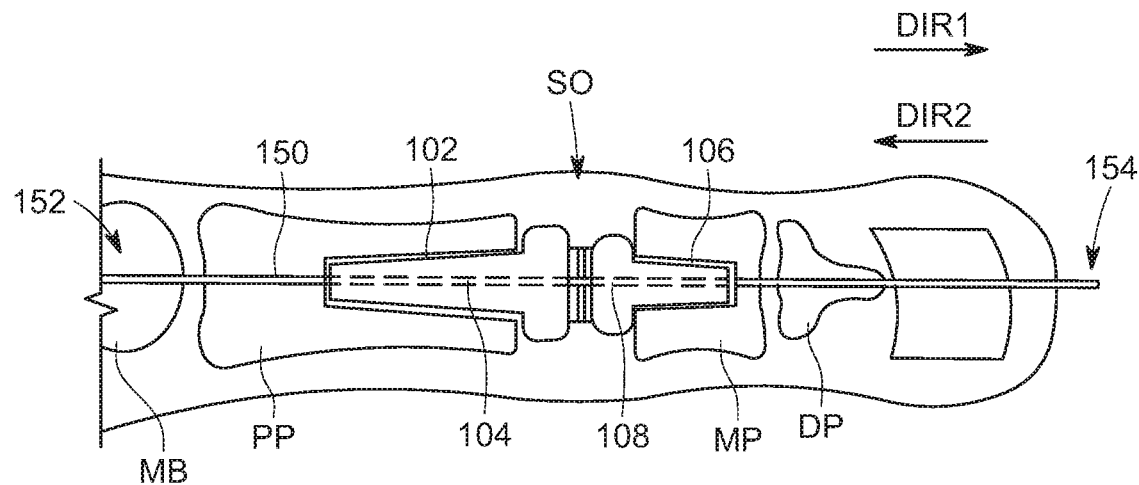
FIG. 5B shows another cross-sectional top plan view of the flexible implant and the elongated pin shown in FIG. 5A.

Referring to FIGS. 3A and 3B, in one embodiment, the implant 100 may be placed in a straight configuration so that the proximal and distal conduits 104, 108 of the respective proximal and distal stems 102, 106 are in alignment with one another (e.g., the proximal and distal conduits are aligned along a common axis $A_1$). After the proximal and distal conduits are aligned, an elongated pin 150 (e.g., a sterilized metal pin) may be passed through the distal conduit 108 of the distal stem 106 and the proximal conduit 104 of the proximal stem 102. The elongated pin 150 is preferably straight and desirably has a proximal end 152 and a distal end 154. The elongated pin may be used to immobilize the joint to allow for post-operative healing. In one embodiment, the elongated pin 150 may be a Kirschner wire (also referred to as a K-wire), which is a sterilized, sharpened, smooth metal (e.g., stainless steel) pin. Introduced in 1909 by Martin Kirschner, the wires are now widely used in orthopedics and other types of medical and veterinary surgery. Kirschner wires come in different sizes and are used to hold bone fragments together (e.g., pin fixation) or to provide an anchor for skeletal traction. The pins are often driven into the bone through the skin (percutaneous pin fixation) such as by using a power tool or a hand drill. https://en.wikipedia.org/wiki/Kirschner_wire.

The elongate pin 150 may have different diameters. In one embodiment, the elongated pin 150 has a diameter of about 0.028-0.062 inches (0.7 mm-1.6 mm). In one embodiment, the elongated pin has a diameter of about 0.045 inches (1.1 mm) or 0.062 inches (1.6 mm).

In one embodiment, the elongated pin 150 preferably passes between the first and second sidewalls 130, 132 that define the topside 128 of the flexible hinge 110. The elongated pin 150 preferably passes through the respective first and second openings 144, 146 (FIG. 2) provided in the opposing first and second sidewalls 130, 132. In one embodiment, the first and second openings 144, 146 are preferably disposed between the top side of the flexible hinge and the upper end of the implant 100.

Referring to FIGS. 4A-4B and 5A-5B, in one embodiment, the implant 100 is desirably used to treat a toe T having a hammertoe deformity, whereby the toe T includes a metatarsal bone MB, a proximal phalanx PP, a middle phalanx MP, and a distal phalanx DP. In one embodiment, a surgical opening SO (FIG. 4B) may be formed in the top of the toe T to expose the proximal end of the middle phalanx MP and the distal end of the proximal phalanx PP.

In one embodiment, a distal implant hole is preferably formed in the proximal end face of the middle phalanx MP such as by using one or more drill bits and a surgical drill. In one embodiment the drilled distal implant hole may initially have a circular cross-section. In one embodiment, a broaching tool may be inserted into the distal implant hole to re-shape the drilled distal implant hole from one having a circular cross-section to one having a square and/or rectangular shaped cross-section that is adapted to seat the square and/or rectangular shaped distal stem 106 of the implant. Squaring off the distal implant hole in the proximal end face of the middle phalanx MP preferably prevents the implant 100 from rotating after the distal stem 106 of the implant 100 has been inserted into the middle phalanx MP.

In one embodiment, a proximal implant hole is preferably formed in the distal end face of the proximal phalanx PP such as by using one or more drill bits and a surgical drill. In one embodiment the drilled proximal implant hole may initially have a circular cross-section. In one embodiment, a broaching tool may be inserted into the proximal implant hole to re-shape the drilled proximal implant hole from one having a circular cross-section to one having a square and/or rectangular shaped cross-section that is adapted to seat the square and/or rectangular shaped proximal stem 102 of the implant. Squaring off the proximal implant hole in the distal end face of the proximal phalanx PP preferably prevents the implant 100 from rotating after the proximal stem 102 of the implant 100 has been inserted into the proximal phalanx PP.

In one embodiment, after the distal stem 106 of the implant 100 has been inserted into the squared-off distal hole formed in the middle phalanx MP and after the proximal stem 102 of the implant 100 has been inserted into the squared-off proximal hole formed in the proximal phalanx PP, the elongated pin 150 is preferably utilized for securing the implant 100 to the bones of the toe T. In one embodiment, in order to secure the implant 100 in place, the distal end 154 of the elongated pin 150 is preferably inserted into the opening 146 in the second sloping sidewall 132 (FIG. 2) at the proximal end of the distal stem 106 of the implant 100. The distal end 154 of the elongated pin 150 is preferably advanced in series in a distal direction designated DIR1 through the distal conduit 108 of the distal stem 106, beyond the distal end of the middle phalanx MP, and through the distal phalanx DP until the distal end 154 of the elongated pin 150 is exposed outside the distal end of the toe T.

In one embodiment, after the distal end 154 of the elongated pin 150 is advanced distally beyond the distal end of the toe T, the direction of the elongated pin is reversed for being advanced in the proximal direction designated DIR2 through the proximal stem 102 of the implant 100. In one embodiment, the proximal end 152 of the elongated pin 150 is preferably inserted into the opening 144 in the first sloping sidewall 130 (FIG. 2) at the distal end of the proximal stem 102 of the implant 100. The proximal end 152 of the elongated pin 150 is preferably advanced in series in a proximal direction through the proximal conduit 104 of the proximal stem 106, beyond the proximal end of the proximal phalanx PP, and into the distal head of the metatarsal bone MB.

The elongated pin 150 preferably secures the implant 100 to the bone and the toe T, holds the implant 100 in a straight configuration during healing, and stabilizes the digital deformity post-operatively. In one embodiment, the centrally placed elongated pin 150 may be removed about 4-6 weeks after the completion of the surgical procedure to allow for flexion at the proximal interphalangeal joint.

Figure 6A:
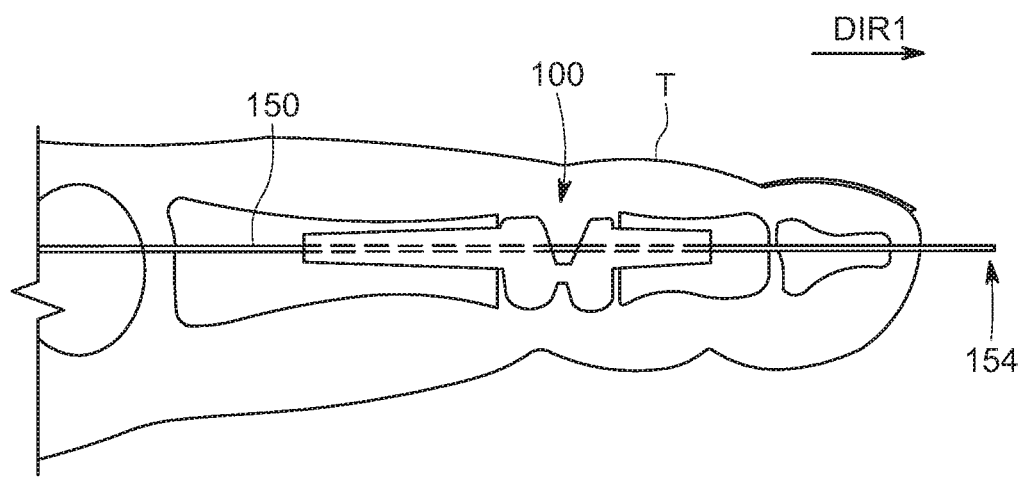
FIG. 6A shows a cross-sectional side view of a method of treating a hammertoe deformity, in accordance with one embodiment of the present patent application.
Figure 6B:
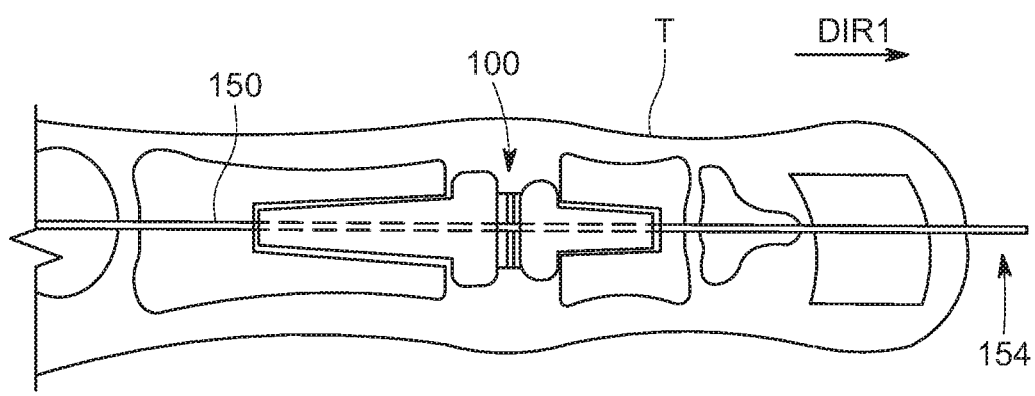
FIG. 6B shows a cross-section top plan view of the method step shown in FIG. 6A.

Referring to FIGS. 6A and 6B, about four-six weeks following completion of a surgical procedure, the elongated pin 150 may be removed to allow the implant 100 to flex. In one embodiment, the distal end 154 of the elongated pin 150 is grasped and pulled in the distal direction designated DIR1 for withdrawing the elongated pin from the bones of the toe T and the implant 100.

Figure 7A:
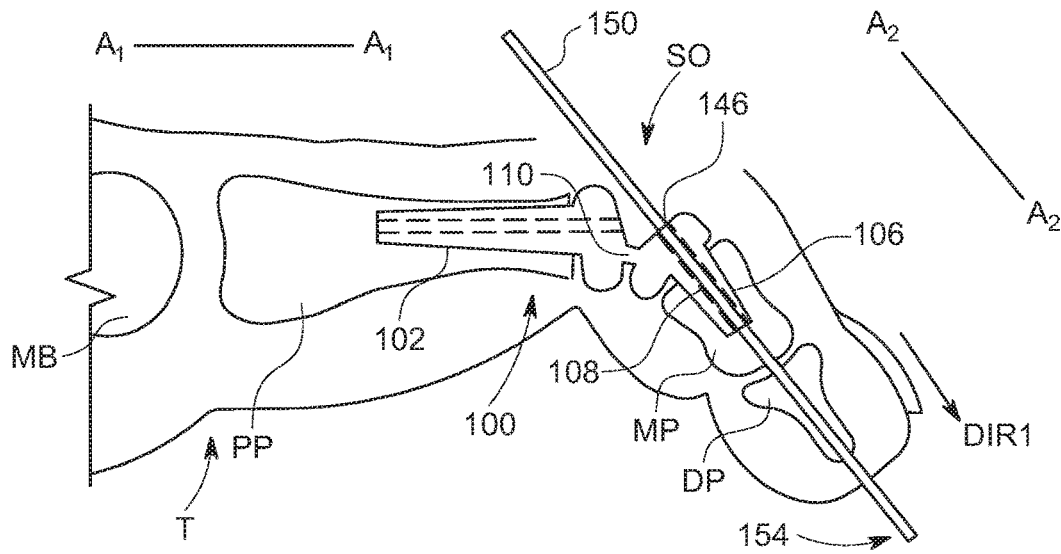
FIG. 7A shows a first step of a method of implanting a flexible implant in a toe, in accordance with one embodiment of the present patent application.

Referring to FIG. 7A, in one embodiment, a flexible implant 100 is desirably used to treat a toe T having a hammertoe deformity, whereby the toe T includes a metatarsal bone MB, a proximal phalanx PP, a middle phalanx MP, and a distal phalanx DP. In other embodiments, the implant may be placed between any two bones in a human or animal body to repair a joint and allow for post-operative flexibility, such as between two bones in a human hand. In one embodiment, a surgical opening SO may be formed in the top of the toe T to expose the proximal end of the middle phalanx MP and the distal end of the proximal phalanx PP.

In one embodiment, a distal implant hole is preferably formed in the proximal end face of the middle phalanx MP such as by using one or more drill bits and a surgical drill. In one embodiment the drilled distal implant hole may initially have a circular cross-section. In one embodiment, a broaching tool may be inserted into the distal implant hole to re-shape the drilled distal implant hole from one having a circular cross-section to one having a square and/or rectangular shaped cross-section that is adapted to seat the square and/or rectangular shaped distal stem 106 of the implant 100. Squaring off the distal implant hole in the proximal end face of the middle phalanx MP preferably prevents the implant 100 from rotating after the distal stem 106 of the implant 100 has been inserted into the middle phalanx MP.

In one embodiment, a proximal implant hole is preferably formed in the distal end face of the proximal phalanx PP such as by using one or more drill bits and a surgical drill. In one embodiment the drilled proximal implant hole may initially have a circular cross-section. In one embodiment, a broaching tool may be inserted into the proximal implant hole to re-shape the drilled proximal implant hole from one having a circular cross-section to one having a square and/or rectangular shaped cross-section that is adapted to seat the square and/or rectangular shaped proximal stem 102 of the implant. Squaring off the proximal implant hole in the distal end face of the proximal phalanx PP preferably prevents the implant 100 from rotating after the proximal stem 102 of the implant 100 has been inserted into the proximal phalanx PP.

In one embodiment, after the distal stem 106 of the implant 100 has been inserted into the squared-off distal hole formed in the middle phalanx MP and the proximal stem 102 of the implant 100 has been inserted into the squared-off proximal hole formed in the proximal phalanx PP, the elongated pin 150 (e.g., a K-wire) is preferably utilized for securing the implant 100 to the bones of the toe T. The elongated pin 150 is preferably straight and rigid and may be made of metals such as biocompatible metals, stainless steel, titanium and/or alloys thereof. In one embodiment, in order to secure the implant 100 in place during healing, the implant 100 may be flexed so that the distal stem 106 extends along an axis $A_2$ and the proximal stem 102 extends along an axis $A_1$ that defines an angle with the axis $A_2$ (e.g., not parallel). With the distal stem 106 angulated relative to the proximal stem 102, the opening 146 in the second sloping sidewall 132 (FIG. 2) of the hinge 110 is accessible through the surgical opening SO, whereupon the distal end 154 of the elongated pin 150 may be inserted into the opening 146. The distal end 154 of the elongated pin 150 is preferably advanced in series in a distal direction designated DIR1 through the distal conduit 108 of the distal stem 106, beyond the distal end of the middle phalanx MP, and through the distal phalanx DP until the distal end 154 of the elongated pin 150 is exposed outside the distal end of the toe T.

Figure 7B:
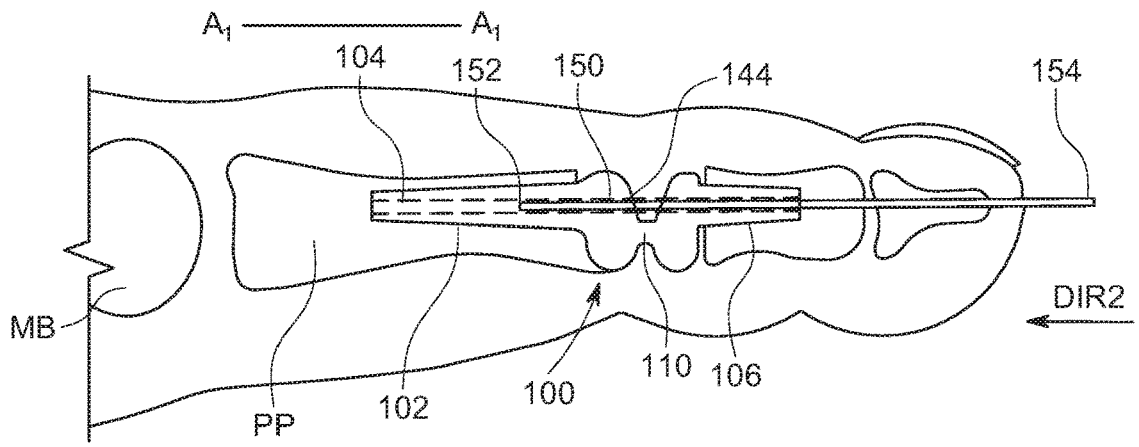
FIG. 7B shows a second step of a method of implanting a flexible implant in a toe, in accordance with one embodiment of the present patent application.
Figure 7C:
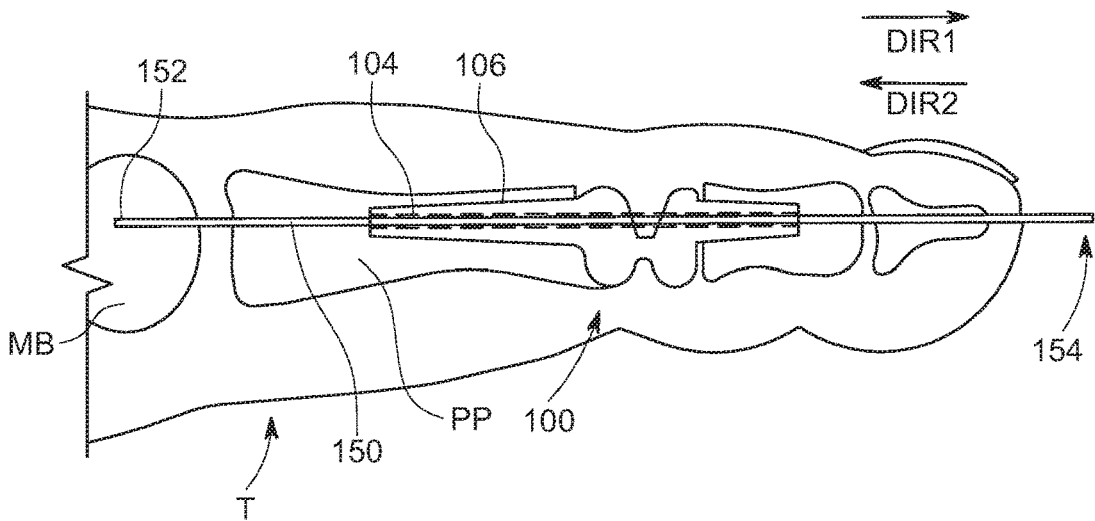
FIG. 7C shows a third step of a method of implanting a flexible implant in a toe, in accordance with one embodiment of the present patent application.

Referring to FIGS. 7A and 7B, in one embodiment, after the distal end 154 of the elongated pin 150 is advanced distally beyond the distal end of the toe T, the direction of the elongated pin may be reversed for being advanced through the proximal stem 102 of the implant 100 in the proximal direction designated DIR2 (FIG. 7B). In one embodiment, with the proximal end 152 of the elongated pin 150 positioned within the V-shaped groove located above the flexible hinge 110, the implant is returned from the flexed configuration shown in FIG. 7A to a straight configuration shown in FIG. 7B. In the straight configuration of FIG. 7B, the proximal and distal stems 102, 106 extend along a common axis $A_1$. In one embodiment, the proximal end 152 of the elongated pin 150 is inserted into the opening 144 in the first sloping sidewall 130 (FIG. 2) of the hinge 110 (at the distal end of the proximal stem 102 of the implant 100). Referring to FIGS. 7B and 7C, the proximal end 152 of the elongated pin 150 is preferably advanced in series in a proximal direction DIR2 through the proximal conduit 104 of the proximal stem 106, beyond the proximal end of the proximal phalanx PP, and into the distal head of the metatarsal bone MB.

The elongated pin 150 preferably secures the implant 100 to the bone and the toe T, holds the implant 100 in a straight configuration during healing, and stabilizes the digital deformity post-operatively. Referring to FIG. 7C, about four-six weeks following completion of a surgical procedure, the elongated pin 150 may be removed to allow the implant 100 to flex. In one embodiment, the distal end 154 of the elongated pin 150 is grasped and pulled in the distal direction designated DIR1 for withdrawing the elongated pin from the bones of the toe T and the implant 100.

Figure 8:
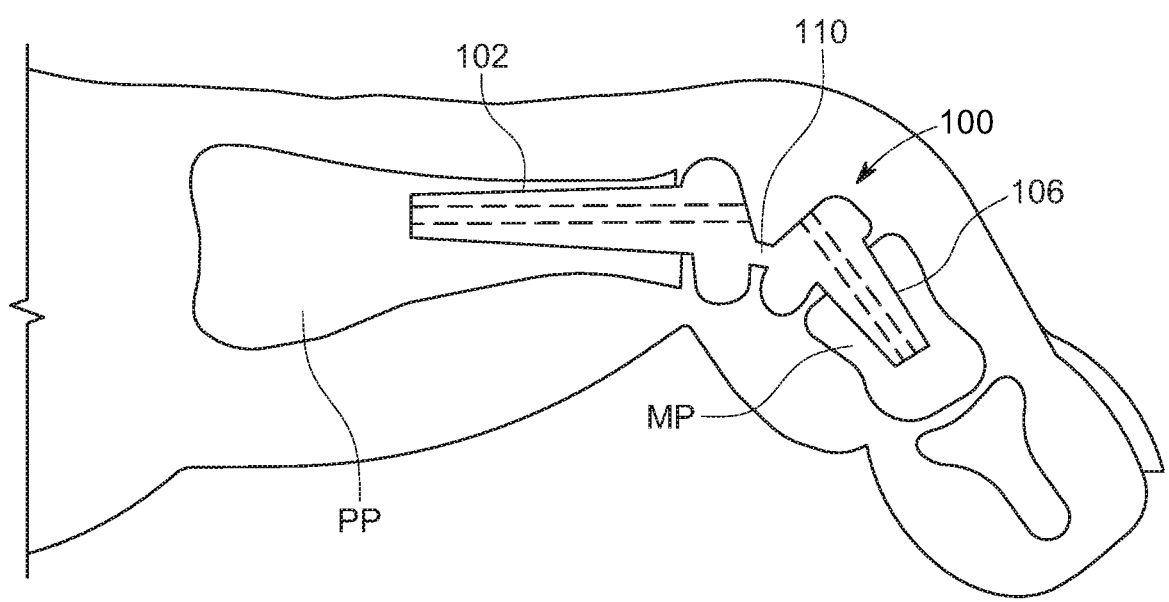
FIG. 8 shows a cross-sectional side view of a flexed toe having the flexible implant of FIG. 7C, in accordance with one embodiment of the present patent application.

Referring to FIG. 8, in one embodiment, after the elongated pin has been removed, the flexible hinge 110 of the implant 100 enables to distal stem 106 of the implant, which is anchored to the middle phalanx MP, to rotate, swing and/or move relative to the proximal stem 102 of the implant 100, which is anchored to the proximal phalanx PP.

Figure 9:
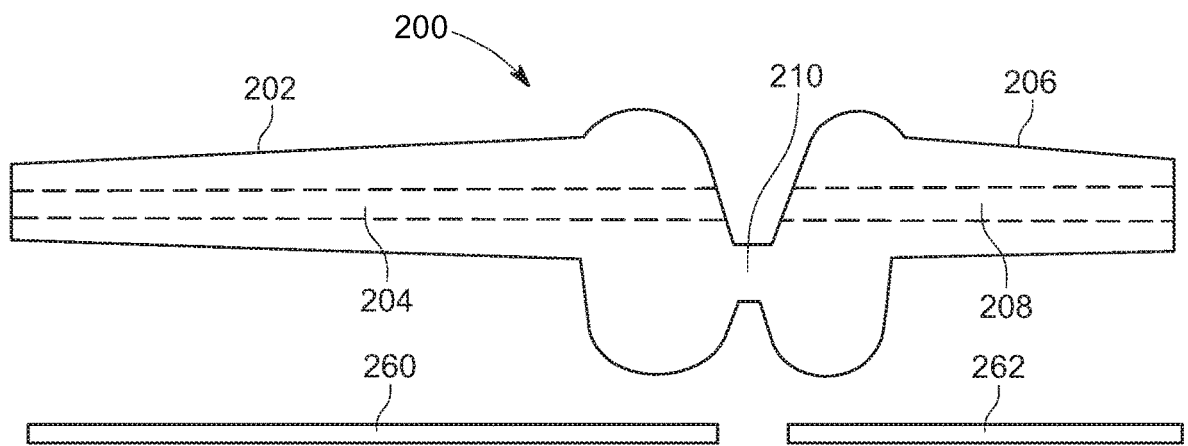
FIG. 9 shows an exploded view of a flexible, cannulated implant having a proximal stem, a proximal protective tube insertable into a proximal conduit of the proximal stem, a distal stem, a distal protective tube insertable into a distal conduit of the distal stem, and a flexible hinge that interconnects the proximal and distal stems, in accordance with one embodiment of the present patent application.

Referring to FIG. 9, in one embodiment, a flexible, cannulated implant 200 preferably includes a proximal stem 202 having a proximal conduit 204 extending therethrough, a distal stem 206 having a distal conduit 208 extending therethrough, and a flexible hinge 210 that is located between and interconnects a distal end of the proximal stem 202 and a proximal end of the distal stem 206. The implant may be implanted in the bones of a patient such as toe and finger bones. In one embodiment, the implant 200 desirably comprises a unitary body including the proximal and distal stems and the flexible hinge. In one embodiment, the unitary body may be molded and may be made of polymers or plastics. In one embodiment, the proximal stem and the proximal conduit associated therewith have a greater length than the distal stem and the distal conduit associated therewith. The flexible hinge 210 preferably enables the implant 200 to flex and/or bend so that after the implant has been implanted in bone (e.g., between bones in a toe, between bones in a finger), the distal stem 206 (e.g., anchored to a middle phalanx MP) may rotate, swing and/or move relative to the proximal stem 202 (anchored to a proximal phalanx PP).

In one embodiment, the implant 200 preferably includes a proximal stem protective tube 260 that is adapted to be inserted into the proximal conduit 204 of the proximal stem 202. In one embodiment, the proximal stem 202 is made of a medical grade, biocompatible polymer and the proximal stem protective tube 260 is made of metal such as stainless steel or titanium. The proximal stem protective tube 260 made of metal preferably prevents the proximal end 152 of an elongated pin 150 (FIG. 7B) from piercing through the polymer or plastic proximal stem as the elongated pin is advanced proximally through the proximal conduit 204 of the proximal stem 202.

In one embodiment, the implant 200 preferably includes a distal stem protective tube 262 that is adapted to be inserted into the distal conduit 208 of the distal stem 206. In one embodiment, the distal stem 206 is made of a medical grade, biocompatible polymer and the distal stem protective tube 262 is made of metal such as stainless steel or titanium. The distal stem protective tube 262 made of metal preferably prevents the distal end 154 of an elongated pin 150 (FIG. 7B) from piercing through the polymer distal stem 206 as the elongated pin is advanced distally through the distal conduit of the distal stem 202.

Figure 10:
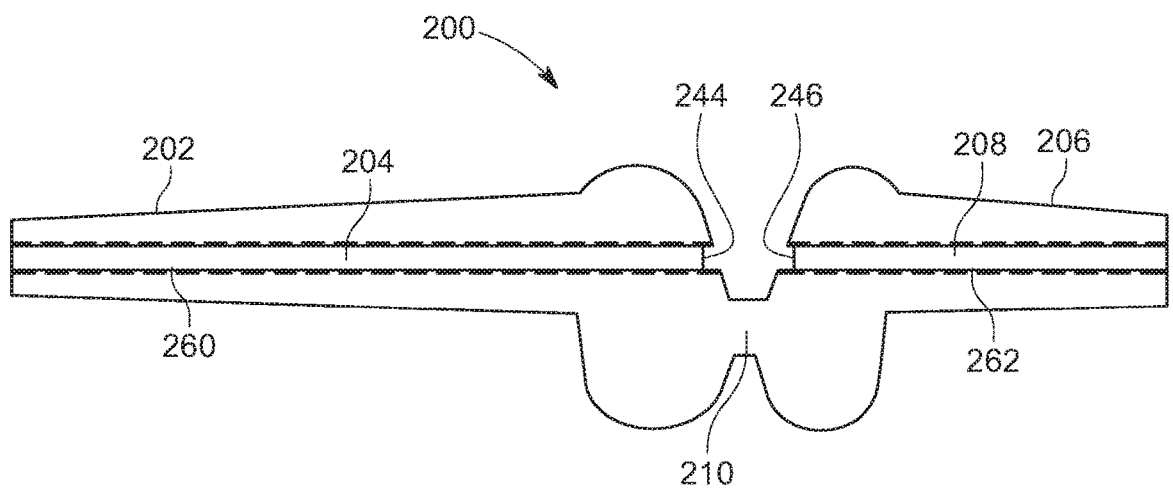
FIG. 10 shows the flexible, cannulated implant of FIG. 9 with the proximal protective tube inserted into the proximal stem and the distal protective tube inserted into the distal stem of the implant.

Referring to FIG. 10, in one embodiment, the proximal stem protective tube 260 is inserted into the proximal conduit 204 of the proximal stem 202 of the implant 200, and the distal stem protective tube 262 is inserted into the distal conduit 208 of the distal stem 206. In one embodiment, the proximal stem protective tube 260 has a length that matches the length of the proximal conduit 204 of the proximal stem 202, and the distal stem protective tube 262 has a length that matches the length of the distal conduit 208 of the distal stem 206. In one embodiment, the proximal stem protective tube 260 is longer than the distal stem protective tube 262. In one embodiment, after assembly with the stems, the respective protective tubes have central openings that are aligned with the first and second openings 244, 246 located above the flexible hinge 210.

Figure 11:
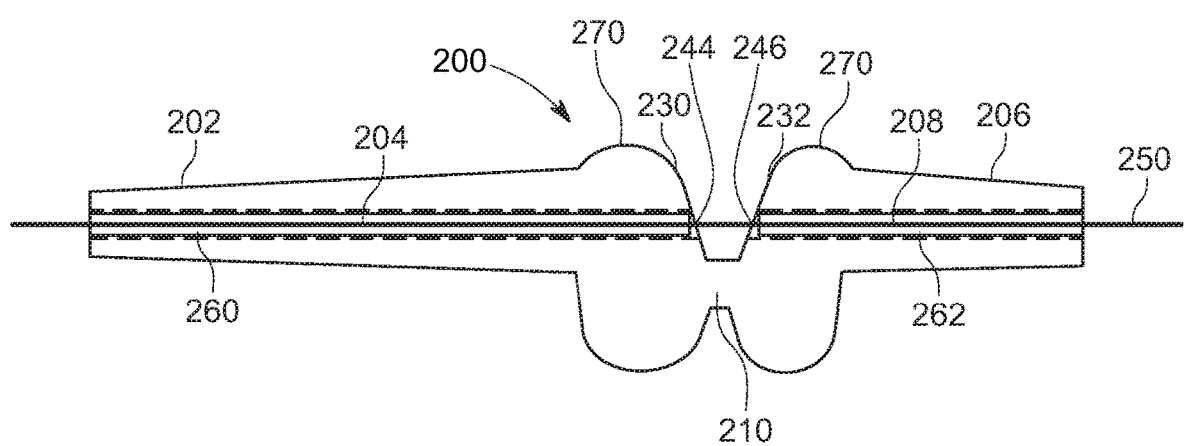
FIG. 11 shows the flexible, cannulated implant of FIG. 10 with an elongated wire extending through the proximal and distal stems of the implant, in accordance with one embodiment of the present patent application.

Referring to FIG. 11, in one embodiment, an elongated pin 250 is adapted to pass through the proximal stem 202 and the distal stem 206 of the implant 200 for securing the implant to bone for post-operative healing, and for holding the implant in a straight configuration during the post-operative healing period. In one embodiment, the implant has a flexible hinge 210 including a first sloping sidewall 230 having an opening 244 aligned with the proximal conduit 204 and an opposing second sloping sidewall 232 having an opening 246 aligned with the distal conduit 208. In one embodiment, the openings 244, 246 are preferably located above a top side of the hinge 210 so that the elongated pin is located between the top side of the hinge 210 and an upper end 270 of the implant 200. As the elongated pin 250 is passed through the implant, the proximal stem protective tube 260 (disposed within proximal conduit 204) and the distal stem protective tube 262 (disposed within distal conduit 208) desirably prevent sharp features on the elongated pin 250 from scraping, scratching, marring, and/or damaging the implant 200, which could adversely impact the reliability, ruggedness and/or performance of the implant 200. For example, a scratch formed in a conduit 204, 208 of a polymer implant may eventually result in the formation of a crack or fissure in the body of the implant, which may have a deleterious impact on the performance of the implant (e.g., require the implant to be removed and replaced).

Figure 12A:
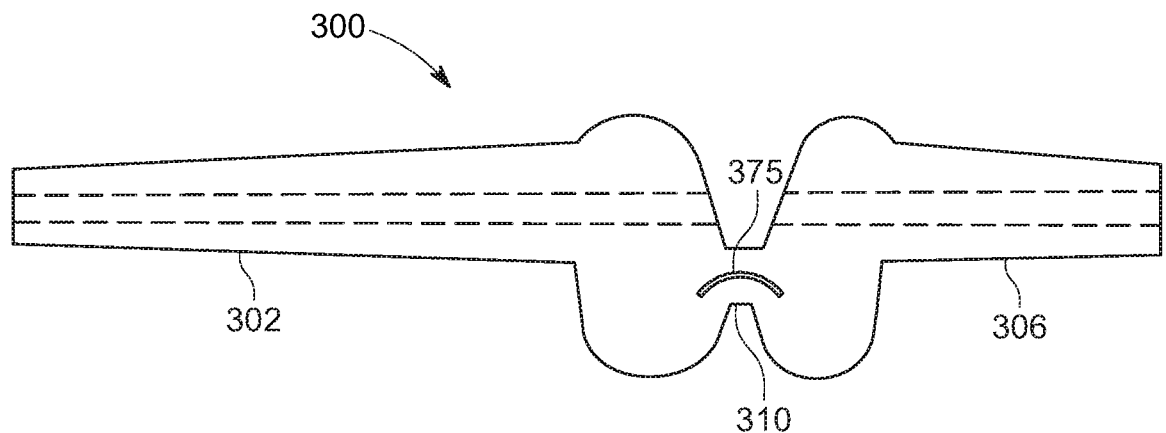
FIG. 12A shows a flexible, cannulated implant having a flexible hinge with a reinforcing element embedded within the flexible hinge, in accordance with one embodiment of the present patent application.
Figure 12B:
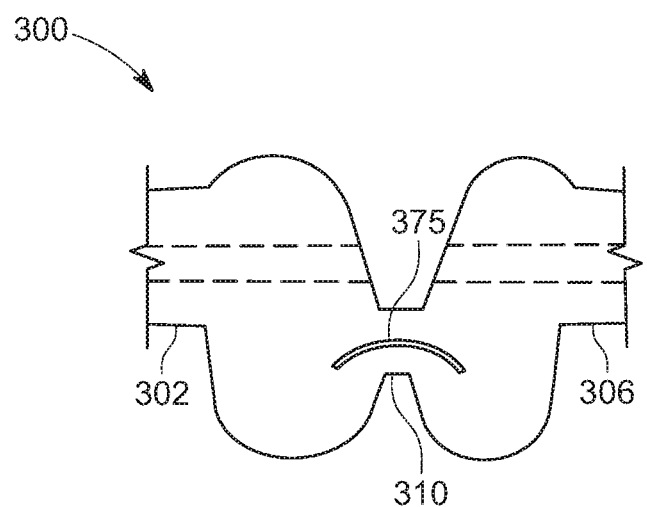
FIG. 12B shows a magnified view of the flexible hinge shown in FIG. 12A.

Referring to FIGS. 12A and 12B, in one embodiment, a flexible implant 300 desirably includes a unitary body made of polymer materials having a proximal stem 302, a distal stem 306 and a flexible hinge 310 that interconnects the proximal and distal stems 302, 306 for enabling the proximal and distal stems to flex and bend relative to one another for providing flexibility to a joint located between adjacent bones. In one embodiment, the flexible implant 300 preferably includes a reinforcing element 375 embedded within the flexible hinge 310 for enhancing the structural integrity of the flexible hinge and preventing the flexible hinge from fracturing when flexing and bending. In one embodiment, the reinforcing element 375 may be a fabric piece. In one embodiment, the reinforcing element 375 may be a mesh, such as a polyester mesh. In one embodiment, the polyester mesh may be made of the polyester fabric sold under the trademark DACRON. In other embodiments, other reinforcing fabrics may be used instead of polyester fabrics so long as they are compatible with the polymer or plastic materials used to make the implant 300.

Figure 13A:
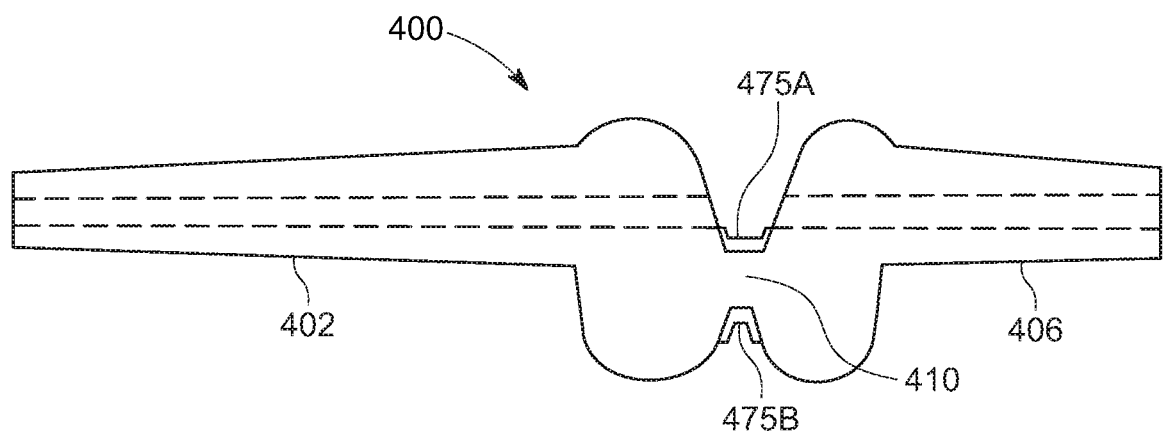
FIG. 13A shows a flexible, cannulated implant having a flexible hinge with reinforcing elements overlying top and bottom surfaces of the flexible hinge, in accordance with one embodiment of the present patent application.
Figure 13B:
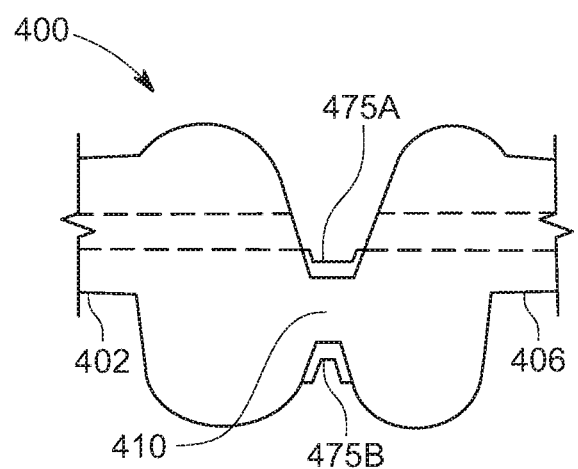
FIG. 13B shows a magnified view of the flexible hinge shown in FIG. 13A.

Referring to FIGS. 13A and 13B, in one embodiment, a flexible implant 400 desirably includes a unitary body made of polymer materials having a proximal stem 402, a distal stem 406 and a flexible hinge 410 that interconnects the proximal and distal stems 402, 406 for enabling the proximal and distal stems to flex and bend relative to one another for providing flexibility to a joint located between adjacent bones. In one embodiment, the flexible implant 400 preferably includes a first reinforcing element 475A overlying a top surface of the flexible hinge 410 and a second reinforcing element 475B overlying a bottom surface of the flexible hinge 410 for enhancing the structural integrity of the flexible hinge and preventing the flexible hinge from fracturing when flexing and bending. In one embodiment, the first and second reinforcing elements 475A, 475B may be fabric pieces, a mesh, a polyester mesh, a polyester fabric sold under the trademark DACRON, and/or other reinforcing fabrics may be used instead of polyester fabrics so long as they are compatible with the polymer or plastic materials used to make the implant 400.

Figure 14A:
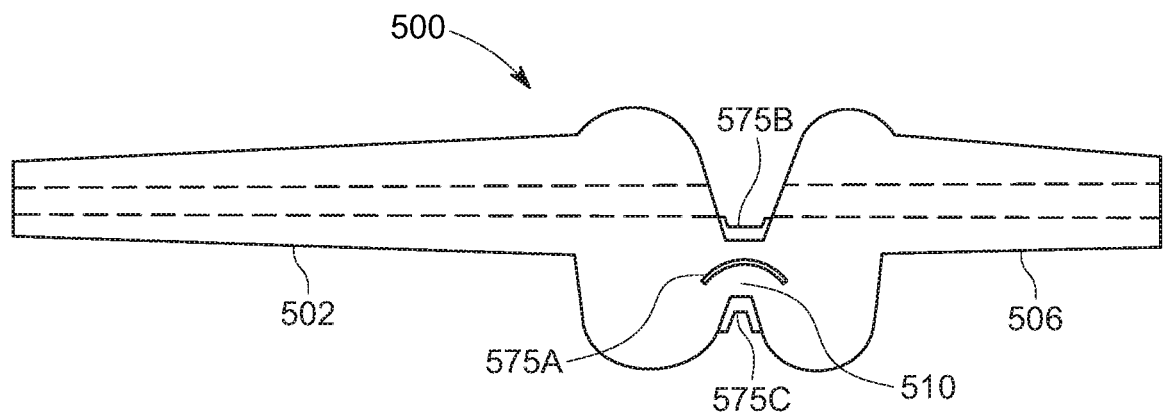
FIG. 14A shows a flexible, cannulated implant having a flexible hinge with a first reinforcing element embedded within the flexible hinge, a second reinforcing element overlying a top surface of the flexible hinge and a third reinforcing element overlying a bottom surface of the flexible hinge, in accordance with one embodiment of the present patent application.
Figure 14B:
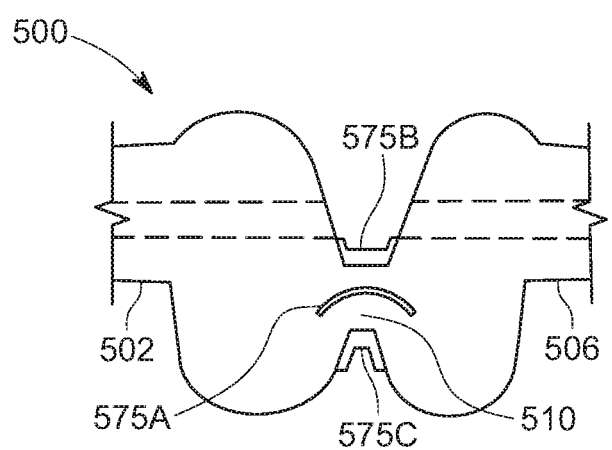
FIG. 14B shows a magnified view of the flexible hinge shown in FIG. 14A.

Referring to FIGS. 14A and 14B, in one embodiment, a flexible implant 500 desirably includes a unitary body made of polymer materials having a proximal stem 502, a distal stem 506 and a flexible hinge 510 that interconnects the proximal and distal stems 502, 506 for enabling the proximal and distal stems to flex and bend relative to one another for providing flexibility to a joint located between adjacent bones. In one embodiment, the flexible implant 500 preferably includes a first reinforcing element 575A embedded within the flexible hinge 510, a second reinforcing element 575B overlying a top surface of the flexible hinge 510, and a third reinforcing element 575C overlying a bottom surface of the flexible hinge 510 for enhancing the structural integrity of the flexible hinge and preventing the flexible hinge from fracturing when flexing and bending. In one embodiment, the reinforcing elements 575A-575C may be fabric pieces, a mesh, a polyester mesh, a polyester fabric sold under the trademark DACRON, and/or other reinforcing fabrics may be used instead of polyester fabrics so long as they are compatible with the polymer or plastic materials used to make the implant 400.

The reinforcing elements shown and described in FIGS. 12A-12B, 13A-13B, and 14A-14B may be incorporated into any of the flexible implants disclosed in the present patent application.

In one embodiment, the implants disclosed herein may be used in the hand and/or for hand digital implantation.

In one embodiment, the implants disclosed herein may be used to treat humans.

In one embodiment, the implants disclosed herein may be used to treat animals having skeletal systems.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A flexible interphalangeal bone implant comprising:
a proximal stem having a proximal end, a distal end, and a proximal conduit having a length extending from the proximal end to the distal end of said proximal stem, wherein said proximal conduit is open at both the proximal and distal ends of said proximal stem;
a distal stem having a proximal end, a distal end, and a distal conduit having a length extending from the proximal end to the distal end of said distal stem, wherein said distal conduit is open at both the proximal and distal ends of said distal stem;
a flexible hinge interconnecting the distal end of said proximal stem with the proximal end of said distal stem for allowing said proximal and distal stems to flex relative to one another, wherein said flexible hinge comprises a top side defined by a first sloping sidewall at the distal end of said proximal stem, a second sloping sidewall at the proximal end of said distal stem that opposes said first sloping sidewall, and a flat top surface that extends between and interconnects lower ends of said first and second sloping sidewalls;

a discrete proximal stem protective tube disposed within said proximal conduit of said proximal stem, wherein said proximal stem protective tube has a length that matches the length of said proximal conduit; and a discrete distal stem protective tube disposed within said distal conduit of said distal stem, wherein said distal stem protective tube has a length that matches the length of said distal conduit;

wherein the proximal and distal stem protective tubes are sized and configured to receive an elongated pin extending in series through said proximal stem protective tube disposed within said proximal stem, said first sloping sidewall, said second sloping sidewall, and said distal stem protective tube disposed within said distal stem;

wherein said proximal stem, said distal stem, and said flexible hinge comprise a unitary structure monolithically made of a polymer material, and wherein said proximal stem protective tube and said distal stem protective tube are made of metal.

2. The flexible interphalangeal bone implant as claimed in claim 1, further comprising an elongated pin extending through said distal stem protective tube disposed within said distal stem and said proximal stem protective tube disposed within said proximal stem.

3. The flexible interphalangeal bone implant as claimed in claim 2, wherein said elongated pin is selected from the group consisting of bone pins and Kirschner wires.

4. The flexible interphalangeal bone implant as claimed in claim 1, wherein said polymer material is selected from the group consisting of silicone elastic polymers and plastics and said metal is selected from the group consisting of biocompatible metals, titanium, titanium alloys, stainless steel, and stainless steel alloys.

5. The flexible interphalangeal bone implant as claimed in claim 1, wherein said proximal stem has a flat top surface, a flat bottom surface, and flat side surfaces that define a proximal stem structure having a substantially square or rectangular shaped cross-section, and wherein said distal stem has a flat top surface, a flat bottom surface, and flat side surfaces that define a distal stem structure having a substantially square or rectangular shaped cross-section.

6. The flexible interphalangeal bone implant as claimed in claim 1, wherein said first sloping sidewall, said second sloping sidewall and said flat top surface define a V-shaped top side of said flexible hinge having a truncated, flat apex.

7. The flexible interphalangeal bone implant as claimed in claim 1, wherein said proximal conduit extending through said proximal stem defines a first opening in said first sloping sidewall, and wherein said distal conduit extending through said distal stem defines a second opening in said second sloping sidewall that is aligned with said first opening in said first sloping sidewall.

8. The flexible interphalangeal bone implant as claimed in claim 7, wherein said flexible implant is normally in a straight configuration in which said proximal and distal conduits extend along a common axis, and wherein said flexible implant is moveable into a flexed configuration in which said proximal and distal conduits extend along different axes that define an angle.

9. The flexible interphalangeal bone implant as claimed in claim 1, wherein said flexible implant further comprises a fabric reinforcing element embedded within said flexible hinge or covering one or more surfaces of said flexible hinge.

10. The flexible interphalangeal bone implant as claimed in claim 1, wherein said flexible hinge comprises a bottom side defined by a first bottom side sloping sidewall at the distal end of said proximal stem, a second bottom side sloping sidewall at the proximal end of said distal stem that opposes said first bottom side sloping sidewall, and a flat bottom surface that extends between and interconnects upper ends of said first and second bottom side sloping sidewalls.

11. The flexible interphalangeal bone implant as claimed in claim 1, wherein said first bottom side sloping sidewall, said second bottom side sloping sidewall, and said flat bottom surface of said bottom side of said flexible hinge preferably define a V-shaped bottom side having a truncated, flat apex.

12. The flexible interphalangeal bone implant as claimed in claim 11, wherein when rotating said distal stem of said implant in a clockwise direction relative to said proximal stem, said second bottom side sloping surface abuts against said first bottom side sloping surface for acting as a hard stop and limiting further rotation of said distal stem relative to said proximal stem.

* * * * *